US012240960B2

(12) United States Patent
Kramer et al.

(10) Patent No.: US 12,240,960 B2
(45) Date of Patent: Mar. 4, 2025

(54) THIXOTROPIC AGENT FOR CURABLE COMPOSITIONS

(71) Applicant: SIKA TECHNOLOGY AG, Baar (CH)

(72) Inventors: Andreas Kramer, Zürich (CH); Urs Burckhardt, Zürich (CH); Michael Schlumpf, Stallikon (CH); Martin Konstanzer, Aarau (CH)

(73) Assignee: SIKA TECHNOLOGY AG, Baar (CH)

( * ) Notice: Subject to any disclaimer, the term of this patent is extended or adjusted under 35 U.S.C. 154(b) by 901 days.

(21) Appl. No.: 17/281,311

(22) PCT Filed: Nov. 11, 2019

(86) PCT No.: PCT/EP2019/080856
§ 371 (c)(1),
(2) Date: Mar. 30, 2021

(87) PCT Pub. No.: WO2020/099314
PCT Pub. Date: May 22, 2020

(65) Prior Publication Data
US 2022/0041838 A1     Feb. 10, 2022

(30) Foreign Application Priority Data
Nov. 14, 2018 (EP) .................... 18206318

(51) Int. Cl.
C08K 5/21       (2006.01)
C07C 273/18     (2006.01)
C08K 5/06       (2006.01)
C09K 3/10       (2006.01)

(52) U.S. Cl.
CPC .............. C08K 5/21 (2013.01); C08K 5/06 (2013.01); C09K 3/10 (2013.01); C07C 273/1818 (2013.01); C09K 2003/1071 (2013.01)

(58) Field of Classification Search
CPC ... C08K 5/21; C08K 5/06; C09K 3/10; C09K 2003/1071; C07C 273/1818
See application file for complete search history.

(56) References Cited

U.S. PATENT DOCUMENTS

| 2002/0007003 A1 | 1/2002 | Merz et al. |
| 2007/0066721 A1 | 3/2007 | Kramer et al. |

FOREIGN PATENT DOCUMENTS

| EP | 1152019 A1 | 11/2001 |
| JP | S59-109553 A | 6/1984 |
| JP | H05-295073 A | 11/1993 |
| JP | 2001-172513 A | 6/2001 |
| JP | 2003-214987 A | 7/2003 |
| JP | 2008-544074 A | 12/2008 |

OTHER PUBLICATIONS

Jan. 23, 2020 International Search Report issued in International Patent Application No. PCT/EP2019/080856.
May 18, 2021 International Preliminary Report on Patentability issued in International Patent Application No. PCT/EP2019/080856.

Primary Examiner — Angela C Scott
(74) Attorney, Agent, or Firm — Oliff PLC

(57) ABSTRACT

A thixotropic agent for increasing the yield point of a curable composition, wherein the thixotropic agent includes (i) at least one urea compound from the reaction of at least one isocyanate with at least one amine and (ii) at least one polyether having blocked hydroxyl groups. The thixotropic agent is preparable in a simple manner and forms a spreadable paste which is firm at room temperature. It is particularly suitable as a constituent of moisture-curing polyurethane or SMP compositions, giving a good increase in the yield point thereof, without adversely affecting storage stability or migration characteristics. It enables phthalate-free adhesives, sealants or coatings that have surprisingly good conveyability coupled with a high yield point, and do not cause any problems with odor or fogging.

15 Claims, No Drawings

THIXOTROPIC AGENT FOR CURABLE COMPOSITIONS

TECHNICAL FIELD

The invention relates to thixotropic agents and to curable compositions thickened therewith, especially elastic adhesives, sealants or coatings.

STATE OF THE ART

In curable compositions based on polyurethane polymers or silane-modified polymers (SMPs), what are called thixotropic agents are often used in order to increase the yield point and hence sag resistance thereof, and hence improve the processability of the products. For pasty adhesives and sealants in particular, important factors are a high sag resistance coupled with not too high an expression force and short threading when the application tool is set down. Particularly effective and inexpensive thixotropic agents are fine dispersions of urea compounds, especially reaction products of diisocyanates with primary amines of low molecular weight, which are produced in a liquid carrier material and are homogeneous, spreadable pastes. The content of urea compounds therein is typically only about twenty percent, as a result of which a relatively large amount of paste is needed for a good thixotropic effect and a correspondingly large amount of carrier material is introduced into the product to be thickened. This can lead to problems with migration effects, such as, in particular, bleeding or staining, especially in the case of porous substrates, or softening, cracking, discoloration or loss of adhesion of the substrate or of a varnish or paint layer applied thereon. On contact with solvents or blowing agents, there can be swelling, followed by the washout of the carrier material, which can lead to cracking and embrittlement of the polymer matrix. In addition, the carrier material can evaporate in the course of heating and hence lead to outgassing losses (fogging).

Suitable carrier materials for such thixotropic pastes are especially the customary plasticizers used in adhesives and sealants for adjustment of hardness and elasticity. Particularly suitable plasticizers are phthalates of relatively high molecular weight, especially diisodecyl phthalate (DIDP) or diisononyl phthalate (DINP). They enable very finely divided pastes which have good thickening, and cause only a low level of migration effects. On contact with alkalis, for example on application to fresh concrete or as a result of basic formulation constituents, however, they can be hydrolyzed and cause embrittlement or depolymerization, often in conjunction with odor emissions emanating from the fatty alcohols used. They also disproportionately increase the stiffness or modulus of elasticity of an adhesive and sealant under cold conditions compared to room temperature. And finally, owing to widespread skepticism with respect to phthalates, there is additionally a desire for phthalate-free products. Alternatives to the phthalate plasticizers are especially cyclohexanedicarboxylic esters, for example diisononyl cyclohexane-1,2-dicarboxylate (DINCH), or adipates, for example dioctyl adipate or bis(2-ethylhexyl) adipate (DOA). However, these show a distinctly higher tendency to migration effects and, when hydrolyzed, likewise release intensely odorous fatty alcohols. They are therefore not very suitable as carrier material. EP 1 152 019 describes thixotropic agents based on urea compounds that use polyols rather than plasticizers as carrier material. The resultant pastes are highly viscous and difficult to handle, especially difficult to pump, and their effect on sag resistance is much smaller than in the pastes based on conventional plasticizers. Since the polyols react with compositions containing isocyanate groups, they do not cause any migration effects, but lead to a significant increase in viscosity, which is disadvantageous for good processability and threading when the application tool for the products thickened therewith is set down.

SUMMARY OF THE INVENTION

It is therefore an object of the present invention to provide a thixotropic agent based on urea compounds for curable compositions based on polyurethane or SMP for increasing the yield point, which is free of phthalates and overcomes the disadvantages of the prior art in relation to increase in viscosity and tendency to migration or fogging.

The object is achieved by the thixotropic agent as described in claim 1. The thixotropic agent is preparable from base materials of good availability in a simple process, is unreactive with respect to isocyanate and silane groups and is of excellent quality. Compared to conventional thixotropic agents based on urea compounds, the thixotropic agent of the invention increases the yield point of compositions thickened therewith to the same or even a higher degree, does not cause any significant tendency to migration effects, and does not release any volatile, intensely odorous cleavage products on saponification or hydrolysis of the carrier material. Surprisingly, the thixotropic agent of the invention, given the same concentration, preparation and sag resistance, is even more easily expressible (lower expression force through a nozzle of a few millimeters), which means that compositions thickened therewith have particularly good processability. Moreover, the cured compositions show particularly good flexibility under cold conditions.

The thixotropic agent of the invention, even in the case of low dosage, shows high thixotropic action, i.e. increase in yield point or sag resistance, and does not lead either to an increase in occurrence of effects caused by plasticizer migration, such as bleeding or staining, or to elevated fogging. It is especially suitable for use in adhesives, sealants or coatings based on polyurethane or SMP, which are preferably phthalate-free.

Further aspects of the invention are the subject of further independent claims. Particularly preferred embodiments of the invention are the subject of the dependent claims.

Ways of Executing the Invention

The invention provides a thixotropic agent for increasing the yield point of a curable composition, wherein the thixotropic agent comprises (i) at least one urea compound from the reaction of at least one isocyanate with at least one amine and (ii) at least one polyether having blocked hydroxyl groups which is free of urethane groups.

A "blocked hydroxyl group" refers to a hydroxyl group converted by chemical reaction to a group unreactive toward isocyanate groups.

"Polyether" refers to a molecule or a group of oligomeric and/or polymeric molecules that consist mainly of repeat alkyleneoxy units.

A "primary amino group" refers to an amino group which is bonded to a single organic radical and bears two hydrogen atoms; a "secondary amino group" refers to an amino group which is bonded to two organic radicals which may also together be part of a ring and bears one hydrogen atom; and a "tertiary amino group" refers to an amino group which is bonded to three organic radicals, two or three of which may also be part of one or more rings, and does not bear any hydrogen atom.

A "primary monoamine" refers to a compound having one primary amino group, which does not have any further amino groups.

A "curable composition" refers to a composition containing polymerizable macromolecules, which, through crosslinking reactions of its reactive groups, can cure or attain a state of elevated mechanical strength.

A "silane group" refers to a silyl group bonded to an organic radical and having one to three, especially two or three, hydrolyzable alkoxy radicals on the silicon atom.

"Silane" refers both to organoalkoxysilanes bearing one to three organic substituents on each silane group and tetraalkoxysilanes. Silanes that bear one or more hydroxyl, isocyanato, amino or mercapto groups in addition to the silane group on an organic radical are referred to as "hydroxysilane", "isocyanatosilane", "aminosilane" and "mercaptosilane" respectively.

"Plasticizer" refers to nonvolatile substances that lower the viscosity of a polymer, are not chemically incorporated within the polymer, and exert a plasticizing effect thereon.

Substance names beginning with "poly", such as polyamine, polyol or polyisocyanate, refer to substances containing, in a formal sense, two or more of the functional groups that occur in their name per molecule.

"Molecular weight" refers to the molar mass (in g/mol) of a molecule or a molecule residue. "Average molecular weight" refers to the number-average molecular weight $M_n$ of a polydisperse mixture of oligomeric or polymeric molecules or molecule residues. It is typically determined by means of gel permeation chromatography (GPC) against polystyrene as standard.

A curable composition referred to as "storage-stable" or "storable" is one that can be stored at room temperature in a suitable container over a prolonged period, typically over at least 3 months up to 6 months or more, without this storage resulting in any change in its application or use properties to an extent relevant to its use.

"Room temperature" refers to a temperature of 23° C.

The thixotropic agent preferably comprises a urea compound from the reaction of at least one diisocyanate with at least one primary monoamine. The amino groups are preferably used stoichiometrically here in relation to the isocyanate groups.

Preferred diisocyanates are hexamethylene 1,6-diisocyanate, 1-isocyanato-3,3,5-trimethyl-5-isocyanatomethylcyclohexane, perhydro(diphenylmethane 4,4'-diisocyanate), phenylene 1,3-diisocyanate, phenylene 1,4-diisocyanate, tolylene 2,4-diisocyanate or mixtures thereof with tolylene 2,6-diisocyanate (TDI), or diphenylmethane 4,4'-diisocyanate, with or without fractions of diphenylmethane 2,4'- and/or 2,2'-diisocyanate (MDI).

Particular preference is given to tolylene 2,4-diisocyanate or diphenylmethane 4,4'-diisocyanate.

Most preferred is diphenylmethane 4,4'-diisocyanate.

This affords particularly effective thixotropic agents.

A preferred primary monoamine is an alkylamine, especially an alkylamine having 1 to 12 carbon atoms. Particular preference is given to an alkylamine having 4 to 6 carbon atoms, especially butylamine, hexylamine or cyclohexylamine.

Most preferred is n-butylamine. This affords particularly effective thixotropic agents.

Particularly preferred urea compounds are reaction products of diphenylmethane 4,4'-diisocyanate and n-butylamine.

The urea compound preferably has the formula (I)

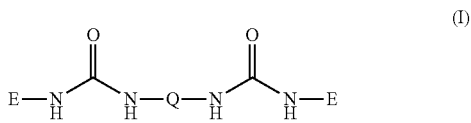

where

E is an alkyl or cycloalkyl radical having 1 to 12 carbon atoms, and

Q is a divalent hydrocarbyl radical having 6 to 15 carbon atoms.

E is preferably an alkyl or cycloalkyl radical having 4 to 6 carbon atoms, especially butyl or hexyl or cyclohexyl.

Most preferably, E is butyl, especially n-butyl.

Q is preferably 1,6-hexylene, (1,5,5-trimethylcyclohexan-1-yl)methane-1,3, methylenebis(cyclohexan-4-yl), 1,3-phenylene, 1,4-phenylene, 4(2)-methyl-1,3-phenylene or methylenebis(phen-4-yl).

More preferably, Q is 4-methyl-1,3-phenylene or methylenebis(phen-4-yl).

Most preferably, Q is methylenebis(phen-4-yl).

The thixotropic agent is preferably prepared by conducting the reaction between the isocyanate and amine in the polyether having blocked hydroxyl groups. The reaction is preferably conducted at a temperature in the range from 0 to 100° C., especially 10 to 80° C.

In the preparation of the thixotropic agent, it is advantageous to use a method in which the reactants used and the reaction mixture are stirred and/or conveyed such that the resultant urea compounds precipitate out in very finely divided form, in order to give rise to a paste of maximum homogeneity with high thixotropic action.

The polyether having blocked hydroxyl groups can be initially charged together with the isocyanate, and the amine can be added gradually with good stirring.

In addition, the polyether having blocked hydroxyl groups can be initially charged together with the amine, and the isocyanate can be added gradually with good stirring.

In addition, the amine and/or the isocyanate can be diluted before use with a little polyether having blocked hydroxyl groups.

The urea compounds are preferably prepared in a continuous process, wherein the amine and/or the isocyanate is optionally used in a form diluted with polyether having blocked hydroxyl groups.

The preparation is preferably performed with exclusion of moisture.

There are preferably no further additives present in the preparation, especially no added solvents and no added catalysts.

The thixotropic agent is preferably in the form of a spreadable paste which is firm at room temperature.

The thixotropic agent preferably contains 5% to 25% by weight of urea compounds and 50% to 95% by weight of polyether having blocked hydroxyl groups.

The thixotropic agent more preferably contains 10% to 25% by weight of urea compounds and 75% to 90% by weight of polyether having blocked hydroxyl groups.

The polyether having blocked hydroxyl groups is essentially free of unblocked hydroxyl groups. What is meant here by "essentially free" is that 95%, preferably 99%, especially 99.9%, most preferably 100%, of the hydroxyl groups present are blocked.

The polyether having blocked hydroxyl groups is preferably free of reactive groups that enter into crosslinking reactions with moisture or with ingredients present in the composition. It is thus especially free of isocyanate groups and silane groups.

The polyether having blocked hydroxyl groups is especially liquid at room temperature.

The polyether having blocked hydroxyl groups preferably has a viscosity at 20° C. in the range from 30 to 500 mPa s, especially 50 to 250 mPa·s. The viscosity is determined here with a cone-plate viscometer having cone diameter 25 mm, cone angle 1°, cone tip-plate distance 0.05 mm, at a shear rate of 10 s$^{-1}$. This affords pastes that are easy to handle and have high thixotropic action.

The polyether preferably has an average of 1 to 3 blocked hydroxyl groups per molecule, especially 1 or 2.

The blocked hydroxyl groups are preferably selected from the group consisting of acetal, ester, aceto ester and carbonate groups.

These acetal, ester, aceto ester or carbonate groups preferably have 1 to 15 carbon atoms.

Particular preference is given to an ester group, especially an ester group having 1 to 8 carbon atoms.

Most preferred is an acetate group. A polyether having blocked hydroxyl groups in the form of acetate groups is of particularly low viscosity, is obtainable in a particularly simple manner and is particularly inexpensive.

A preferred acetal group is a 1-(isobutoxy)ethoxy or a tetrahydropyran-2-oxy or a tetrahydrofuran-2-oxy group, especially a 1-(isobutoxy)ethoxy group.

A preferred aceto ester group is an acetoacetate group.

A preferred carbonate group is a methyl carbonate group.

These are of low viscosity and obtainable from inexpensive raw materials.

Repeat units present in the polyether having blocked hydroxyl groups are preferably 1,2-ethyleneoxy, 1,2-propyleneoxy, 1,3-propyleneoxy, 1,2-butyleneoxy or 1,4-butyleneoxy groups, especially 1,2-propyleneoxy groups.

Preferably, 70% to 100% by weight, especially 80% to 100% by weight, of the repeat units consist of 1,2-propyleneoxy groups, and 0% to 30% by weight, especially 0% to 20% by weight, of the repeat units consist of 1,2-ethyleneoxy groups.

More preferably, the repeat units consist entirely of 1,2-propyleneoxy groups. Such polyethers are readily available and hydrophobic, and enable thixotropic curable compositions having low water absorption and good stability.

The polyether having blocked hydroxyl groups preferably has an average molecular weight $M_n$ in the range from 600 to 2,500 g/mol, more preferably 700 to 2,000 g/mol, especially 800 to 1,500 g/mol, determined by means of gel permeation chromatography (GPC) against polystyrene as standard with tetrahydrofuran as mobile phase, refractive index detector and evaluation from 200 g/mol. This affords pastes that are easy to handle and have high thixotropic action, and do not cause any problems with emission or odor in curable compositions.

The polyether having blocked hydroxyl groups is preferably derived from at least one hydroxy-functional polyether selected from the group consisting of
alcohol-started, especially n-butanol-started, polyoxypropylene monools having an OH number in the range from 25 to 90 mg KOH/g, preferably 50 to 80 mg KOH/g,
polyoxypropylene diols having an OH number in the range from 45 to 155 mg KOH/g, preferably 56 to 125 mg KOH/g, and
trimethylolpropane- or especially glycerol-started, optionally ethylene oxide-terminated polyoxypropylene triols having an average OH functionality in the range from 2.2 to 3 and an OH number in the range from 90 to 230 mg KOH/g.

Among these, preference is given to alcohol-started, especially n-butanol-started, polyoxypropylene monools or polyoxypropylene diols.

Particular preference is given to polyoxypropylene diols. These are particularly inexpensive.

The polyether having blocked hydroxyl groups is especially obtained by reacting at least one hydroxy-functional polyether with at least one suitable blocking agent for hydroxyl groups.

For the reaction, the blocking agent is used at least stoichiometrically in relation to the hydroxyl groups, such that the hydroxyl groups are essentially completely blocked and the polyether obtained is thus essentially free of hydroxyl groups. For the blocking, methods customary for the respective reactive groups are used, optionally with additional use of catalysts or solvents. If the blocking reaction forms elimination products, these are removed from the reaction mixture by a suitable method, especially by means of distillation.

Suitable blocking agents are nucleophilic compounds that enter into an addition or substitution reaction with hydroxyl groups.

Especially suitable are vinyl ethers, carboxylic acids, carbonyl chlorides, carboxylic esters or carboxylic anhydrides, diketene, 2,2,5-trimethyl-4H-1,3-dioxin-4-one, alkyl acetoacetates, dialkyl carbonates, (meth)acrylamides, methylenemalonates or cyanoacrylates.

Preference is given to vinyl ethers such as, in particular, methyl vinyl ether, ethyl vinyl ether, isopropyl vinyl ether, butyl vinyl ether, isobutyl vinyl ether, isopropenyl methyl ether, isopropenyl ethyl ether, 2,3-dihydrofuran or 3,4-dihydro-2H-pyran, more preferably isobutyl vinyl ether, 2,3-dihydrofuran or 3,4-dihydro-2H-pyran, with formation of blocked hydroxyl groups in the form of acetal groups. The reaction is preferably conducted in the presence of an acid as catalyst, especially hydrochloric acid, sulfuric acid, phosphoric acid or a sulfonic acid, optionally in the form of an acidic ion exchange resin.

Preference is also given to carboxylic acids, carbonyl chlorides, carboxylic esters or carboxylic anhydrides, with formation of blocked hydroxyl groups in the form of ester groups. Among these, preference is given to carboxylic anhydrides or carboxylic esters, especially acetic anhydride.

In the case of acetic anhydride as blocking agent, the reaction releases acetic acid, with formation of blocked hydroxyl groups in the form of acetate groups.

In the case of isopropenyl acetate as blocking agent, the reaction releases acetone, likewise with formation of blocked hydroxyl groups in the form of acetate groups.

Preference is further given to diketene, 2,2,5-trimethyl-4H-1,3-dioxin-4-one or sterically hindered alkyl acetoacetates such as, in particular, tert-butyl acetoacetate, with formation of blocked hydroxyl groups in the form of aceto ester groups.

Preference is further given to dialkyl carbonates, especially dimethyl carbonate, with formation of blocked hydroxyl groups in the form of carbonate groups, especially methyl carbonate groups.

Suitable hydroxy-functional polyethers are especially those having an average OH functionality in the range from 1 to 3 and an average molecular weight $M_n$ in the range from 500 to 2,500 g/mol, more preferably 600 to 2,000 g/mol, especially 700 to 1,500 g/mol.

Preference is given to polyoxypropylene monools having an OH number in the range from 25 to 90 mg KOH/g, preferably 50 to 80 mg KOH/g, especially alcohol-started polyoxypropylene monools, especially started from methanol, ethanol, propanol, isopropanol, n-butanol, isobutanol, tert-butanol, pentanol, hexanol, 2-ethylhexanol, lauryl alcohol, myristyl alcohol, palmityl alcohol, allyl alcohol, cyclohexanol, benzyl alcohol or phenol. Among these, preference is given to alkyl alcohol-started polyoxypropylene monools, especially started from methanol, ethanol or n-butanol. Particular preference is given to n-butanol-started polyoxypropylene monools having an average molecular weight $M_n$ in the range from 650 to 2,000 g/mol, especially 700 to 1,500 g/mol. n-Butanol-started polyoxypropylene monools are commercially available, for example as Synalox® 100-20B, Synalox® 100-40B or Synalox® 100-85B (all from DowDuPont Inc.). Also preferred are polyoxypropylene diols having an OH number in the range from 45 to 155 mg KOH/g, preferably 56 to 125 mg KOH/g.

Also preferred are trimethylolpropane- or especially glycerol-started, optionally ethylene oxide-terminated polyoxypropylene triols having an average OH functionality in the range from 2.2 to 3 and an OH number in the range from 90 to 230 mg KOH/g.

The preferred polyethers having blocked hydroxyl groups are preparable from readily available base materials in a simple process, are of low viscosity, and enable thixotropic agents that are in paste form and are easy to handle, which surprisingly lead, even in a small amount, to a significant increase in yield point without unduly increasing the viscosity or expressability of the material to be rendered thixotropic.

The invention further provides for the use of the thixotropic agent of the invention in a curable composition for increasing the yield point of the composition, i.e. for rendering the composition thixotropic. This effect is often also referred to as "thickening", although this does not mean an increase in the viscosity, but rather the increasing of the yield point or sag resistance. Such a thixotropic composition can be applied to an inclined substrate or a vertical overhang without flowing away or sagging significantly.

For this use, the thixotropic agent is mixed with the curable composition or with at least one constituent of the curable composition by a suitable method, preferably with exclusion of moisture, optionally under reduced pressure.

Especially the urea compounds present in the thixotropic agent result in the elevated yield point, while the polyether having blocked hydroxyl groups exerts a thinning effect and, after curing, a plasticizing effect on the composition.

A preferred curable composition is a composition containing isocyanate and/or silane groups.

Particular preference is given to curable compositions comprising at least one polymer containing isocyanate and/or silane groups.

The curable composition may be in the form of a one-component composition or in the form of a multi-component, especially two-component, composition.

A composition referred to as a "one-component" composition is one in which all constituents of the composition are in the same container, which is storage-stable per se and which is curable with moisture.

A composition referred to as a "two-component" composition is one in which the constituents of the composition are in two different components which are stored in separate containers and are not mixed with one another until shortly before or during the application of the composition.

The curable composition is preferably a one-component moisture-curing composition. The thixotropic agent of the invention is particularly suitable for one-component compositions. It is storage-stable together therewith under exclusion of moisture.

Particular preference is given to use as thixotropic agent for curable compositions that have particularly good sag resistance and are nevertheless intended to be applicable from a container without any great expenditure of force. Such properties are especially desirable for pasty adhesives and sealants. These are to have good expressability from a cartridge or pumpability out of a hobbock or drum and, due to high sag resistance and short threading, assure uncomplicated and clean application.

The thixotropic agent described enables phthalate-free pasty one-component adhesives and sealants where a cone (nose) having a base area of about 2 to 3 cm and a length of about 5 to 7 cm that protrudes horizontally from a wall remains stationary such that it sags only by a few millimeters after application, measured at the tip.

The invention further provides a curable composition comprising the thixotropic agent of the invention and at least one polymer containing isocyanate and/or silane groups.

The polymer containing isocyanate and/or silane groups preferably has an average molecular weight $M_n$ in the range from 1,000 to 30,000 g/mol, especially 2,000 to 20,000 g/mol.

It is preferably liquid at room temperature.

In a preferred embodiment, the composition contains at least one polymer containing isocyanate groups. Such a composition is also referred to as "polyurethane composition".

A suitable polymer containing isocyanate groups is especially obtained from the reaction of at least one polyol with a superstoichiometric amount of at least one diisocyanate. The reaction is preferably conducted with exclusion of moisture at a temperature in the range from 20 to 160° C., especially 40 to 140° C., optionally in the presence of suitable catalysts.

The NCO/OH ratio is preferably in the range from 1.3/1 to 10/1. The monomeric diisocyanate remaining in the reaction mixture after the reaction of the OH groups can be removed, especially by means of distillation.

If excess monomeric diisocyanate is removed by means of distillation, the NCO/OH ratio in the reaction is preferably in the range from 4/1 to 7/1, and the resultant polymer containing isocyanate groups, after the distillation, preferably contains not more than 0.5% by weight, more preferably not more than 0.3% by weight, of monomeric diisocyanate. Monomeric diisocyanate is especially removed by means of short-path distillation under reduced pressure.

If no excess monomeric diisocyanate is removed from the polymer, the NCO/OH ratio in the reaction is preferably in the range from 1.3/1 to 2.5/1.

The resultant polymer preferably has a content of isocyanate groups in the range from 0.5% to 10% by weight, especially 1% to 5% by weight, more preferably 1 to 3% by weight, and an average molecular weight $M_n$ in the range from 1,500 to 20,000 g/mol, especially 2,000 to 15,000 g/mol.

The polymer is optionally prepared with additional use of plasticizers or solvents, in which case the plasticizers or solvents used do not contain any groups reactive toward isocyanates.

Preference is given to aliphatic, cycloaliphatic or aromatic diisocyanates, especially hexamethylene 1,6-diisocyanate (HDI), 1-isocyanato-3,3,5-trimethyl-5-isocyanatomethylcyclohexane (isophorone diisocyanate or IPDI), perhydro(diphenylmethane 2,4'- and/or 4,4'-diisocyanate) ($H_{12}MDI$), diphenylmethane 4,4'-diisocyanate, with or without fractions of diphenylmethane 2,4'- and/or 2,2'-diisocyanate (MDI), or tolylene 2,4-diisocyanate or mixtures thereof with tolylene 2,6-diisocyanate (TDI).

Particular preference is given to HDI, IPDI, MDI or TDI, or mixtures thereof.

Suitable polyols are commercial polyols or mixtures thereof, especially polyether polyols, especially polyoxyalkylenediols and/or polyoxyalkylenetriols, especially polymerization products of ethylene oxide or 1,2-propylene oxide or 1,2- or 2,3-butylene oxide or oxetane or tetrahydrofuran or mixtures thereof, where these may be polymerized with the aid of a starter molecule having two or three active hydrogen atoms, especially a starter molecule such as water, ammonia or a compound having multiple OH or NH groups, for example ethane-1,2-diol, propane-1,2- or -1,3-diol, neopentyl glycol, diethylene glycol, triethylene glycol, the isomeric dipropylene glycols or tripropylene glycols, the isomeric butanediols, pentanediols, hexanediols, heptanediols, octanediols, nonanediols, decanediols, undecanediols, cyclohexane-1,3- or -1,4-dimethanol, bisphenol A, hydrogenated bisphenol A, 1,1,1-trimethylolethane, 1,1,1-trimethylolpropane, glycerol or aniline, or mixtures of the aforementioned compounds. Likewise suitable are polyether polyols with polymer particles dispersed therein, especially those with styrene/acrylonitrile (SAN) particles or polyurea or polyhydrazodicarbonamide (PHD) particles.

Preferred polyether polyols are polyoxypropylene diols or polyoxypropylene triols, or what are called ethylene oxide-terminated (EO-capped or EO-tipped) polyoxypropylene diols or triols. The latter are mixed polyoxyethylene/polyoxypropylene polyols which are especially obtained in that polyoxypropylene diols or triols, on conclusion of the polypropoxylation reaction, are further alkoxylated with ethylene oxide and hence have primary hydroxyl groups.

Preferred polyether polyols have a level of unsaturation of less than 0.02 meq/g, especially less than 0.01 meq/g.

Polyester polyols, also called oligoesterols, prepared by known processes, especially the polycondensation of hydroxycarboxylic acids or lactones or the polycondensation of aliphatic and/or aromatic polycarboxylic acids with di- or polyhydric alcohols. Preference is given to polyester diols from the reaction of dihydric alcohols, such as, in particular, 1,2-ethanediol, diethylene glycol, 1,2-propanediol, dipropylene glycol, 1,4-butanediol, 1,5-pentanediol, 1,6-hexanediol, neopentyl glycol, glycerol, 1,1,1-trimethylolpropane or mixtures of the aforementioned alcohols, with organic dicarboxylic acids or the anhydrides or esters thereof, such as, in particular, succinic acid, glutaric acid, adipic acid, suberic acid, sebacic acid, dodecanedicarboxylic acid, maleic acid, fumaric acid, phthalic acid, isophthalic acid, terephthalic acid, cyclohexane-1,2-dicarboxylic acid, cyclohexane-1,3-dicarboxylic acid or cyclohexane-1,4-dicarboxylic acid or mixtures of the aforementioned acids, or polyester polyols formed from lactones such as, in particular, ε-caprolactone. Particular preference is given to polyester polyols formed from adipic acid or sebacic acid or dodecanedicarboxylic acid and hexanediol or neopentyl glycol.

Polycarbonate polyols as obtainable by reaction, for example, of the abovementioned alcohols—used to form the polyester polyols—with dialkyl carbonates, diaryl carbonates or phosgene.

Block copolymers bearing at least two OH groups and having at least two different blocks having polyether, polyester and/or polycarbonate structure of the type described above, especially polyether polyester polyols.

Polyacrylate or polymethacrylate polyols.

Polyhydroxy-functional fats or oils, for example natural fats and oils, especially castor oil; or polyols obtained by chemical modification of natural fats and oils—called oleochemical polyols—for example the epoxy polyesters or epoxy polyethers obtained by epoxidation of unsaturated oils and subsequent ring opening with carboxylic acids or alcohols, or polyols obtained by hydroformylation and hydrogenation of unsaturated oils; or polyols obtained from natural fats and oils by degradation processes, such as alcoholysis or ozonolysis, and subsequent chemical linkage, for example by transesterification or dimerization, of the degradation products or derivatives thereof thus obtained. Suitable degradation products of natural fats and oils are in particular fatty acids and fatty alcohols and also fatty acid esters, in particular the methyl esters (FAME), which can be derivatized to hydroxy fatty acid esters, for example by hydroformylation and hydrogenation.

Polyhydrocarbon polyols, also called oligohydrocarbonols, such as, in particular, polyhydroxy-functional polyolefins, polyisobutylenes, polyisoprenes; polyhydroxy-functional ethylene/propylene, ethylene/butylene or ethylene/propylene/diene copolymers, as produced, for example, by Kraton Polymers; polyhydroxy-functional polymers of dienes, especially of 1,3-butadiene, which can especially also be prepared from anionic polymerization; polyhydroxy-functional copolymers of dienes, such as 1,3-butadiene, or diene mixtures and vinyl monomers, such as styrene, acrylonitrile, vinyl chloride, vinyl acetate, vinyl alcohol, isobutylene or isoprene, especially polyhydroxy-functional acrylonitrile/butadiene copolymers, as can be prepared, in particular, from epoxides or amino alcohols and carboxyl-terminated acrylonitrile/butadiene copolymers (commercially available, for example, under the Hypro® CTBN or CTBNX or ETBN name from Emerald Performance Materials); or hydrogenated polyhydroxy-functional polymers or copolymers of dienes.

Also especially suitable are mixtures of polyols.

Preference is given to polyether polyols, polyester polyols, polycarbonate polyols, poly(meth)acrylate polyols or polybutadiene polyols.

Particular preference is given to polyether polyols, polyester polyols, especially aliphatic polyester polyols, or polycarbonate polyols, especially aliphatic polycarbonate polyols.

Especially preferred are polyether polyols, especially polyoxyalkylene polyols. Most preferred are polyoxypropylene di- or triols or ethylene oxide-terminated polyoxypropylene di- or triols.

Preference is given to polyols having an average molecular weight $M_n$ in the range from 400 to 20,000 g/mol, preferably from 1,000 to 15,000 g/mol. Preference is given to polyols having an average OH functionality in the range from 1.6 to 3.

Preference is given to polyols that are liquid at room temperature.

In the preparation of a polymer containing isocyanate groups, it is also possible to use fractions of di- or polyfunctional alcohols, especially ethane-1,2-diol, propane-1,2-diol, propane-1,3-diol, 2-methylpropane-1,3-diol, butane-1,2-diol, butane-1,3-diol, butane-1,4-diol, pentane-1,3-diol, pentane-1,5-diol, 3-methylpentane-1,5-diol, neopentyl glycol, dibromoneopentyl glycol, hexane-1,2-diol, hexane-1,6-diol, heptane-1,7-diol, octane-1,2-diol, octane-1,8-diol, 2-ethylhexane-1,3-diol, diethylene glycol, triethylene glycol, dipropylene glycol, tripropylene glycol, cyclohexane-1,3- or -1,4-dimethanol, ethoxylated bisphenol A, propoxylated bisphenol A, cyclohexanediol, hydrogenated bisphenol A, dimer fatty acid alcohols, 1,1,1-trimethylolethane, 1,1,1-trimethylolpropane, glycerol, pentaerythritol, sugar alcohols, such as especially xylitol, sorbitol or mannitol, or sugars such as, in particular, sucrose, or alkoxylated derivatives of the alcohols mentioned or mixtures of the alcohols mentioned.

The polymer containing isocyanate groups preferably has an average molecular weight $M_n$ in the range from 1,500 to 20,000 g/mol, especially 2,000 to 15,000 g/mol.

In addition to a polymer containing isocyanate groups, the composition may comprise at least one oligomeric isocyanate or a form of MDI that is liquid at room temperature.

Suitable oligomeric isocyanates are especially HDI biurets such as Desmodur® N 100 or N 3200 (from Covestro AG), Tolonate® HDB or HDB-LV (from Vencorex Holding SAS) or Duranate® 24A-100 (from Asahi Kasei Corp.); HDI isocyanurates such as Desmodur® N 3300, N 3600 or N 3790 BA (all from Covestro AG), Tolonate® HDT, HDT-LV or HDT-LV2 (from Vencorex Holding SAS), Duranate® TPA-100 or THA-100 (from Asahi Kasei Corp.) or Coronate® HX (from Tosoh Corp.); HDI uretdiones such as Desmodur® N 3400 (from Covestro AG); HDI iminooxadiazinediones such as Desmodur® XP 2410 (from Covestro AG); HDI allophanates such as Desmodur® VP LS 2102 (from Covestro AG); IPDI isocyanurates, for example in solution as Desmodur® Z 4470 (from Covestro AG) or in solid form as Vestanat® T1890/100 (from Evonik Industries AG); TDI oligomers such as Desmodur® IL (from Covestro AG); or mixed isocyanurates based on TDI/HDI, such as Desmodur® HL (from Covestro AG).

A form of MDI which is liquid at room temperature is either 4,4'-MDI liquefied by partial chemical modification—especially carbodiimidization or uretonimine formation or adduct formation with polyols—or it is a mixture of 4,4'-MDI with other MDI isomers (2,4'-MDI and/or 2,2'-MDI), and/or with MDI oligomers and/or MDI homologs (polymeric MDI or PMDI), that has been brought about selectively by blending or results from the production process.

In a preferred embodiment of the invention, the curable composition comprises, in addition to at least one polymer containing isocyanate groups, at least one latent curing agent. Such polyurethane compositions are particularly less prone to blistering during curing.

Preferred latent curing agents are ketimines, aldimines or oxazolidines, especially oxazolidines or aldimines, most preferably aldimines.

Preference is given to an aldimine of the formula

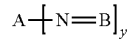

where y is 2 or 3, A is an organic radical having 2 to 23 carbon atoms, and B is an organic radical having 6 to 30 carbon atoms.

A is preferably an alkylene radical optionally having cyclic components or a di- or trivalent polyoxyalkylene radical having 5 to 15 carbon atoms, especially 1,6-hexylene, (1,5,5-trimethylcyclohexan-1-yl)methane-1,3 or α,ω-polyoxypropylene having an average molecular weight $M_n$ in the range from 170 to 300 g/mol or trimethylolpropane-started tris(ω-polyoxypropylene) having an average molecular weight $M_n$ in the range from 330 to 500 g/mol.

B is preferably an organic radical having 7 to 22 carbon atoms, especially 2,2-dimethyl-3-acetoxypropylidene, 2,2-dimethyl-3-lauroyloxypropylidene, 2,2-dimethyl-3-(N-morpholino)propylidene, benzylidene or alkyl-substituted benzylidene, especially 4-decylbenzylidene, 4-undecylbenzylidene, 4-dodecylbenzylidene, 4-tridecylbenzylidene or 4-tetradecylbenzylidene, in which the 4-alkyl radicals are mainly branched.

More preferably, B is a radical having at least 15 carbon atoms, especially 2,2-dimethyl-3-lauroyloxypropylidene or alkyl-substituted benzylidene. Such an aldimine is odorless.

An aldimine of the formula $A\text{---}[B]_y$ is especially obtained by reaction of an amine of the formula $A\text{-}(NH_2)_y$ with an aldehyde of the formula O═B, with removal of water of condensation.

Preferred amines $A\text{-}(NH_2)_y$ are aliphatic or cycloaliphatic primary di- or triamines, especially hexamethylene-1,6-diamine, isophoronediamine, α,ω-polyoxypropylenediamines having an average molecular weight $M_n$ in the range from 200 to 350 g/mol, especially Jeffamine® D-230 (from Huntsman Corp.), or trimethylolpropane-started tris(ω-polyoxypropyleneamine), especially Jeffamine® T-403 (from Huntsman Corp.).

Preferred aldehydes O═B are aldol esters of carboxylic acids, especially 2,2-dimethyl-3-acetoxypropanal, 2,2-dimethyl-3-lauroxyloxypropanal, 2,2-dimethyl-3-(N-morpholino)propanal, benzaldehyde, or benzaldehydes substituted by alkyl radicals, especially 4-decylbenzaldehyde, 4-undecylbenzaldehyde, 4-dodecylbenzaldehyde, 4-tridecylbenzaldehyde or 4-tetradecylbenzaldehyde, in which the 4-alkyl radicals are mainly branched, and mixtures of these benzaldehydes substituted by alkyl radicals.

On contact with moisture, the latent curing agent releases amino groups and possibly hydroxyl groups, which react with isocyanates and act as crosslinkers. This releases an aldehyde or ketone.

In the case of the preferred aldehydes of the formula O═B in which B is a long-chain radical, especially a radical having 15 or more carbon atoms, this does not cause any odor problems and remains in the composition after curing, where it has good compatibility and likewise acts as plasticizer.

Compared to the direct reaction of water with isocyanates, crosslinking via latent curing agents has the advantage that no $CO_2$ is released, which greatly reduces the tendency to formation of blisters in the course of curing.

In a further preferred embodiment, the curable composition contains at least one organic polymer containing silane groups. Such a polymer is also referred to as "silane-modified polymer" (SMP), and such a composition is thus also referred to as an SMP composition.

The organic polymer containing silane groups preferably has silane groups of the formula

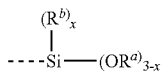

where
$R^a$ is a linear or branched, monovalent hydrocarbyl radical having 1 to 5 carbon atoms, especially methyl or ethyl,
$R^b$ is a linear or branched monovalent hydrocarbyl radical having 1 to 8 carbon atoms, especially methyl, and
x has a value of 0 or 1 or 2, preferably 0 or 1, especially 0.

Methoxysilane groups have the advantage here that they are particularly reactive.

Ethoxysilane groups have the advantage that they are toxicologically advantageous and particularly storage-stable.

Particular preference is given to trimethoxysilane groups, dimethoxymethylsilane groups or triethoxysilane groups.

Most preferred are trimethoxysilane groups or triethoxysilane groups.

A preferred organic polymer containing silane groups is a polyolefin or a polyester or a polyamide or a poly(meth)acrylate or a polyether or a mixed form of these polymers. The silane groups may be in pendant positions in the chain or in terminal positions and are attached to the organic polymer via a carbon atom.

More preferably, the organic polymer containing silane groups is a polyether containing silane groups.

"Polyethers containing silane groups" refer to organic polymers containing at least one silane group, wherein the polymer chain has mainly polyether units, especially 1,2-oxypropylene units. As well as the polyether units, it is especially also possible for there to be urethane groups, urea groups, thiourethane groups, ester groups or amide groups.

The polyether containing silane groups preferably contains at least 50% by weight, especially at least 70% by weight, more preferably at least 80% by weight, of 1,2-oxypropylene units.

Processes for preparing suitable polyethers containing silane groups are known to the person skilled in the art.

In a preferred process, polyethers containing silane groups are obtainable from the reaction with hydrosilanes of polyethers containing allyl groups, optionally with chain extension using for example diisocyanates.

In a further preferred process, polyethers containing silane groups are obtainable from the copolymerization of alkylene oxides and epoxysilanes, optionally with chain extension using for example diisocyanates.

In a further preferred process, polyethers containing silane groups are obtainable from the reaction of polyether polyols with isocyanatosilanes, optionally with chain extension using diisocyanates.

In a further preferred process, polyethers containing silane groups are obtainable from the reaction of polyethers containing isocyanate groups with aminosilanes, hydroxysilanes or mercaptosilanes. Particular preference is given to polyethers containing silane groups from this process. This process enables the use of a multitude of commercially readily available inexpensive starting materials by means of which different polymer properties are obtainable, especially high extensibility, high strength, low modulus of elasticity, low glass transition temperature or high weathering resistance.

More preferably, the polyether containing silane groups is obtainable from the reaction of polyethers containing isocyanate groups with aminosilanes and/or hydroxysilanes and/or mercaptosilanes.

Suitable polyethers containing isocyanate groups are especially obtainable from the reaction of polyether polyols, especially polyoxyalkylene diols or polyoxyalkylene triols, preferably polyoxypropylene diols or polyoxypropylene triols, with a superstoichiometric amount of diisocyanates.

It is preferable when the reaction between the diisocyanate and the polyether polyol is conducted with exclusion of moisture at a temperature of 50° C. to 160° C., optionally in the presence of suitable catalysts, wherein the diisocyanate has been dosed such that the isocyanate groups thereof are present in the stoichiometric excess in relation to the hydroxyl groups of the polyol. In particular, the excess of diisocyanate is chosen so as to leave, after the reaction of all hydroxyl groups, a content of free isocyanate groups of 0.1% to 5% by weight, preferably 0.2% to 4% by weight, more preferably 0.3% to 3% by weight, based on the overall polymer. Preferred diisocyanates are those already mentioned above. Particular preference is given to IPDI or TDI. Most preferred is IPDI. In this way, polyethers containing silane groups with particularly good lightfastness are obtained.

Especially suitable as polyether polyols are polyoxypropylenediols having a degree of unsaturation lower than 0.02 meq/g, especially lower than 0.01 meq/g, and an average molecular weight $M_n$ in the range from 400 to 25,000 g/mol, especially 1,000 to 20,000 g/mol.

In addition to polyether polyols it is also possible to use proportions of other polyols, in particular polyacrylate polyols, and also low-molecular-weight diols or triols.

Suitable aminosilanes for the reaction with a polyether containing isocyanate groups are primary and especially secondary aminosilanes. Preference is given to 3-aminopropyltrimethoxysilane, 3-aminopropyldimethoxymethylsilane, 4-aminobutyltrimethoxysilane, 4-amino-3-methylbutyltrimethoxysilane, 4-amino-3,3-dimethylbutyltrimethoxysilane, N-butyl-3-aminopropyltrimethoxysilane, N-phenyl-3-aminopropyltrimethoxysilane, adducts formed from primary aminosilanes such as 3-aminopropyltrimethoxysilane, 3-aminopropyldimethoxymethylsilane or N-(2-aminoethyl)-3-aminopropyltrimethoxysilane and Michael acceptors such as acrylonitrile, (meth)acrylic esters, (meth)acrylamides, maleic or fumaric diesters, citraconic diesters or itaconic diesters, especially dimethyl or diethyl N-(3-trimethoxysilylpropyl)aminosuccinate. Likewise suitable are analogs of the recited aminosilanes with ethoxy groups in place of the methoxy groups on the silicon.

Suitable hydroxysilanes for the reaction with a polyether containing isocyanate groups are especially obtainable from the addition of aminosilanes onto lactones or onto cyclic carbonates or onto lactides.

Preferred hydroxysilanes that are obtained in this way are N-(3-triethoxysilylpropyl)-2-hydroxypropanamide, N-(3-trimethoxysilylpropyl)-2-hydroxypropanamide, N-(3-triethoxysilylpropyl)-4-hydroxypentanamide, N-(3-triethoxysilylpropyl)-4-hydroxyoctanamide, N-(3-triethoxysilylpropyl)-5-hydroxydecanamide or N-(3-triethoxysilylpropyl)-2-hydroxypropyl carbamate.

Further suitable hydroxysilanes are obtainable from the addition of aminosilanes onto epoxides or from the addition of amines onto epoxysilanes.

Preferred hydroxysilanes that are obtained in this way are 2-morpholino-4(5)-(2-trimethoxysilylethyl)cyclohexan-1-ol, 2-morpholino-4(5)-(2-triethoxysilylethyl)cyclohexan-1-ol or 1-morpholino-3-(3-(triethoxysilyl)propoxy)propan-2-ol.

Suitable mercaptosilanes for the reaction with a polyether containing isocyanate groups are especially 3-mercaptopropyltrimethoxysilane or 3-mercaptopropyltriethoxysilane.

Further suitable polyethers containing silane groups are commercially available products, especially the following: MS Polymer™ (from Kaneka Corp.; especially the S203H, S303H, S227, S810, MA903 and S943 products); MS Polymer™ or Silyl™ (from Kaneka Corp.; especially the SAT010, SAT030, SAT200, SAX350, SAX400, SAX725, MAX450, MAX951 products); Excestar® (from Asahi Glass Co. Ltd.; especially the S2410, S2420, S3430, S3630 products); SPUR+* (from Momentive Performance Materials Inc.; especially the 1010LM, 1015LM, 1050MM products); Vorasil™ (from DowDuPont Inc.; especially the 602 and 604 products); Desmoseal® (from Covestro AG; especially the S XP 2458, S XP 2636, S XP 2749, S XP 2774 and S XP 2821 products), TEGOPAC® (from Evonik Industries AG; especially the Seal 100, Bond 150, Bond 250 products), Polymer ST (from Hanse Chemie AG/Evonik Industries AG, especially the 47, 48, 61, 61 LV, 77, 80, 81 products); Geniosil® STP (from Wacker Chemie AG; especially the E10, E15, E30, E35 products).

More preferably, the polyether containing silane groups is obtained from the reaction of at least one polyether containing isocyanate groups with at least one aminosilane and/or hydroxysilane and/or mercaptosilane.

Preferably, the aminosilane and/or hydroxysilane and/or mercaptosilane here is selected from the group consisting of dimethyl N-(3-trimethoxysilylpropyl)aminosuccinate, diethyl N-(3-trimethoxysilylpropyl)aminosuccinate, dimethyl N-(3-triethoxysilylpropyl)aminosuccinate, diethyl N-(3-triethoxysilylpropyl)aminosuccinate, N-(3-trimethoxysilylpropyl)-2-hydroxypropanamide, N-(3-triethoxysilylpropyl)-2-hydroxypropanamide, 3-mercaptopropyltrimethoxysilane and 3-mercaptopropyltriethoxysilane.

The preferred embodiments of the organic polymer containing silane groups enable compositions having good storage stability, rapid curing and particularly good mechanical properties, especially high elasticity and extensibility coupled with good strength, and high thermal stability.

The curable composition preferably additionally comprises one or more further constituents, especially selected from the group consisting of plasticizers, fillers, adhesion promoters, desiccants and catalysts.

Suitable plasticizers are especially carboxylic acid esters, such as phthalates, especially diisononyl phthalate (DINP), diisodecyl phthalate (DIDP) or di(2-propylheptyl)phthalate (DPHP), hydrogenated phthalates or cyclohexane-1,2-dicarboxylates, especially hydrogenated diisononyl phthalate or diisononyl cyclohexane-1,2-dicarboxylate (DINCH), terephthalates, especially bis(2-ethylhexyl) terephthalate (DOTP) or diisononyl terephthalate (DINT), hydrogenated terephthalates or cyclohexane-1,4-dicarboxylates, especially hydrogenated bis(2-ethylhexyl) terephthalate or bis(2-ethylhexyl) cyclohexane-1,4-dicarboxylate, or hydrogenated diisononyl terephthalate or diisononyl cyclohexane-1,4-dicarboxylate, isophthalates, trimellitates, adipates, especially dioctyl adipate, azelates, sebacates, benzoates, glycol ethers, glycol esters, plasticizers having polyether structure, such as, in particular, the described polyethers having blocked hydroxyl groups, organic phosphoric or sulfonic acid esters, polybutenes, polyisobutenes or plasticizers derived from natural fats or oils, especially epoxidized soybean or linseed oil.

Preferred plasticizers are the described polyethers having blocked hydroxyl groups.

Suitable fillers are especially ground or precipitated calcium carbonates, optionally coated with fatty acids, especially stearates, barytes, quartz flours, quartz sands, dolomites, wollastonites, calcined kaolins, sheet silicates, such as mica or talc, zeolites, aluminum hydroxides, magnesium hydroxides, silicas, including finely divided silicas from pyrolysis processes, cements, gypsums, fly ashes, industrially produced carbon blacks, graphite, metal powders, for example of aluminum, copper, iron, silver or steel, PVC powders or hollow beads.

Preference is given to calcium carbonates that have optionally been coated with fatty acids, especially stearates, calcined kaolins or industrially produced carbon blacks.

Suitable adhesion promoters are especially aminosilanes such as, in particular, 3-aminopropyltrimethoxysilane, 3-aminopropyldimethoxymethylsilane, N-(2-aminoethyl)-3-aminopropyltrimethoxysilane, N-(2-aminoethyl)-3-aminopropyldimethoxymethylsilane, N-(2-aminoethyl)-N'-[3-(trimethoxysilyl)propyl]ethylenediamine or the analogs thereof with ethoxy in place of methoxy groups, and also N-phenyl-, N-cyclohexyl- or N-alkylaminosilanes, mercaptosilanes, epoxysilanes, (meth)acryloylsilanes, anhydridosilanes, carbamatosilanes, alkylsilanes or iminosilanes, oligomeric forms of these silanes, adducts formed from primary aminosilanes with epoxysilanes or (meth)acryloylsilanes or anhydridosilanes, amino-functional alkylsilsesquioxanes, especially amino-functional methylsilsesquioxane or amino-functional propylsilsesquioxane, or titanates.

Especially suitable as adhesion promoters for a composition containing isocyanate groups are epoxysilanes such as, in particular, 3-glycidoxypropyltrimethoxysilane or 3-glycidoxypropyltriethoxysilane, (meth)acryloylsilanes, anhydridosilanes, carbamatosilanes, alkylsilanes or iminosilanes, or oligomeric forms of these silanes.

Suitable desiccants for compositions comprising polymers containing silane groups are especially tetraethoxysilane, vinyltrimethoxysilane, vinyltriethoxysilane or organoalkoxysilanes having a functional group in a position to the silane group, especially N-(methyldimethoxysilylmethyl)-O-methylcarbamate, (methacryloyloxymethyl)silanes, methoxymethylsilanes, orthoformic esters, calcium oxide or molecular sieve powders.

Suitable desiccants for compositions containing isocyanate groups are especially molecular sieve powders, calcium oxide, highly reactive isocyanates such as p-tosyl isocyanate, monomeric diisocyanates or orthoformic esters.

Suitable catalysts are catalysts for the crosslinking of silane groups, especially metal catalysts such as, in particular, compounds of tin, titanium, zirconium, aluminum or zinc, and/or nitrogen compounds. Preference is given to diorganotin(IV) compounds such as, in particular, dibutyltin (IV) diacetate, dibutyltin(IV) dilaurate, dibutyltin(IV) dineodecanoate, dibutyltin(IV) bis(acetylacetonate) or dioctyltin (IV) dilaurate, and also titanium(IV) or zirconium(IV) or aluminum(III) or zinc(II) complexes with, in particular, alkoxy, carboxylate, 1,3-diketonate, 1,3-ketoesterate or 1,3-ketoamidate ligands, especially organotitanates, and also amines, amidines such as, in particular, 1,8-diazabicyclo [5.4.0]undec-7-ene (DBU), 1,5-diazabicyclo[4.3.0]non-5- ene (DBN), 6-dibutylamino-1,8-diazabicyclo[5.4.0]undec-7-ene, 6-dibutylamino-1,8-diazabicyclo[5.4.0]undec-7-ene, N,N'-di-n-hexylacetamidine (DHA), 2-methyl-1,4,5,6-tetrahydropyrimidine, 1,2-dimethyl-1,4,5,6-tetrahydropyrimidine, 2,5,5-trimethyl-1,4,5,6-tetrahydropyrim idine, N-(3-trimethoxysilylpropyl)-4,5-dihydroimidazole, N-(3-triethoxysilylpropyl)-4,5-dihydroimidazole, 1-(3-dimethylaminopropyl)-2-methyl-1,4,5,6-tetrahydropyrimidine, 1-(3-aminopropyl)-2-methyl-1,4,5,6-tetrahydropyrimidine or reaction products thereof, or guanidines such as, in particular, 1-butylguanidine, 1,1-dimethylguanidine, 1,3-dimethylguanidine, 1,1,3,3-tetramethylguanidine (TMG), 2-(3-(trimethoxysilyl)propyl)-1,1,3,3-tetramethylguanidine, 2-(3-(methyldimethoxysilyl)propyl)-1,1,3,3-tetramethylguanidine, 2-(3-(triethoxysilyl)propyl)-1,1,3,3-tetramethylguanidine, 1,5,7-triazabicyclo[4.4.0]dec-5-ene (TBD), 7-methyl-1,5,7-triazabicyclo[4.4.0]dec-5-ene, 7-cyclohexyl-1,5,7-triazabicyclo[4.4.0]dec-5-ene, 1-phenylguanidine, 1-(o-tolyl)guanidine (OTG), 1,3-diphenylguanidine, 1,3-di(o-tolyl)guanidine, 2-guanidinobenzimidazole or guanidines from the reaction of monoamines, polyamines or aminosilanes with carbodiimides, especially dicyclohexylcarbodiimide or diisopropylcarbodiimide, and biguanides or imidazoles.

Preference is given to organotitanates, especially bis(ethylacetoacetato)diisobutoxytitanium(IV) (commercially available, for example, as Tyzor® IBAY from Dorf Ketal), bis(ethylacetoacetato)diisopropoxytitanium(IV) (commercially available, for example, as Tyzor® DC from Dorf Ketal), bis(acetylacetonato)diisopropoxytitanium(IV), bis(acetylacetonato)diisobutoxytitanium(IV), tris(oxyethyl)amineisopropoxytitanium(IV), bis[tris(oxyethyl)amine]diisopropoxytitanium(IV), bis(2-ethylhexane-1,3-dioxy)titanium(IV), tris[24(2-aminoethyl)amino)ethoxy]ethoxytitanium(IV), bis(neopentyl(diallyl)oxy) diethoxytitanium(IV), tetra(isopropoxy)titanate, tetra(n-butoxy)titanate, tetra(2-ethylhexyloxy)titanate or polybutyl titanate, especially bis(ethylacetoacetato)diisobutoxytitanium(IV) or bis(ethylacetoacetato)diisopropoxytitanium(IV).

Preference is further given to amidines or guanidines, especially DBU, 1-(3-dimethylaminopropyl)-2-methyl-1,4,5,6-tetrahydropyrimidine, 1-(3-aminopropyl)-2-methyl-1,4,5,6-tetrahydropyrimidine or reaction products thereof, or guanidines from the reaction of monoamines, polyamines or aminosilanes with dicyclohexylcarbodiimide or diisopropylcarbodiimide.

Preference is further given to combinations of these catalysts, especially combinations of at least one organotitanate and at least one amidine or guanidine.

Suitable catalysts are also catalysts for the acceleration of the reaction of isocyanate groups, especially organotin(IV) compounds, such as especially dibutyltin diacetate, dibutyltin dilaurate, dibutyltin dichloride, dibutyltin diacetylacetonate, dimethyltin dilaurate, dioctyltin diacetate, dioctyltin dilaurate or dioctyltin diacetylacetonate, complexes of bismuth(III) or zirconium(IV), especially with ligands selected from alkoxides, carboxylates, 1,3-diketonates, oxinate, 1,3-ketoesterates and 1,3-ketoamidates, or compounds containing tertiary amino groups, such as especially 2,2'-dimorpholinodiethyl ether (DMDEE).

Suitable catalysts are also catalysts for the hydrolysis of latent curing agents, especially carboxylic acids, such as 2-ethylhexanoic acid, lauric acid, stearic acid, neodecanoic acid, benzoic acid, salicylic acid or 2-nitrobenzoic acid, organic carboxylic anhydrides, silyl esters of carboxylic acids, organic sulfonic acids, sulfonic esters, other organic or inorganic acids, or mixtures of the abovementioned acids or esters. Preference is given to aromatic carboxylic acids such as benzoic acid, 2-nitrobenzoic acid or especially salicylic acid.

The curable composition may contain further additions, especially:
  inorganic or organic pigments, especially titanium dioxide, chromium oxides or iron oxides;
  fibers, especially glass fibers, carbon fibers, metal fibers, ceramic fibers, polymer fibers, such as polyamide fibers or polyethylene fibers, or natural fibers, such as wool, cellulose, hemp or sisal;
  nanofillers such as graphene or carbon nanotubes;
  dyes;
  further catalysts which accelerate the reaction of the isocyanate groups and/or silane groups, especially salts, soaps or complexes of tin(II), iron, aluminum, molybdenum, dioxomolybdenum or potassium, especially aluminum lactate, aluminum oleate or potassium acetate; compounds containing tertiary amino groups, especially N-ethyldiisopropylamine, N,N,N',N'-tetramethylalkylenediamines, pentamethylalkylenetriamines and higher homologs thereof, bis(N,N-diethylaminoethyl) adipate, tris(3-dimethylaminopropyl)amine, 1,4-diazabicyclo[2.2.2]octane (DABCO), N-alkylmorpholines, N,N'-dimethylpiperazine; aromatic nitrogen compounds, such as 4-dimethylaminopyridine, N-methylimidazole, N-vinylimidazole or 1,2-dimethylimidazole; organic ammonium compounds, such as benzyltrimethylammonium hydroxide or alkoxylated tertiary amines; and what are called "delayed action" catalysts, which are modifications of known metal or amine catalysts;
  further rheology modifiers, especially sheet silicates such as bentonites, derivatives of castor oil, hydrogenated castor oil, polyamides, polyurethanes, fumed silicas, cellulose ethers or hydrophobically modified polyoxyethylenes;
  solvents, especially acetone, methyl acetate, tert-butyl acetate, 1-methoxy-2-propyl acetate, ethyl 3-ethoxypropionate, diisopropyl ether, diethylene glycol diethyl ether, ethylene glycol diethyl ether, ethylene glycol monobutyl ether, ethylene glycol mono-2-ethylhexyl ether, acetals such as propylal, butylal, 2-ethylhexylal, dioxolane, glycerol formal or 2,5,7,10-tetraoxaundecane (TOU), toluene, xylene, heptane, octane, naphtha, white spirit, petroleum ether or gasoline, especially Solvesso™ grades (from ExxonMobil Chemical Co.), and propylene carbonate, dimethyl carbonate, butyrolactone, N-methylpyrrolidone, N-ethylpyrrolidone, p-chlorobenzotrifluoride or benzotrifluoride;
  natural resins, fats or oils, such as rosin, shellac, linseed oil, castor oil or soybean oil;
  nonreactive polymers, especially homo- or copolymers of unsaturated monomers, especially from the group comprising ethylene, propylene, butylene, isobutylene, isoprene, vinyl acetate or alkyl (meth)acrylates, especially polyethylenes (PE), polypropylenes (PP), polyisobutylenes, ethylene/vinyl acetate copolymers (EVA) or atactic poly-α-olefins (APAO);
  flame-retardant substances, especially the aluminum hydroxide or magnesium hydroxide fillers already mentioned, and also especially organic phosphoric acid esters, such as especially triethyl phosphate, tricresyl phosphate, triphenyl phosphate, diphenyl cresyl phosphate, isodecyl diphenyl phosphate, tris(1,3-dichloro-2-propyl) phosphate, tris(2-chloroethyl) phosphate, tris(2-ethylhexyl) phosphate, tris(chloroisopropyl)

phosphate, tris(chloropropyl) phosphate, isopropylated triphenyl phosphate, mono-, bis- or tris(isopropylphenyl) phosphates of different degrees of isopropylation, resorcinol bis(diphenylphosphate), bisphenol A bis(diphenylphosphate) or ammonium polyphosphates;

additives, especially wetting agents, leveling agents, defoamers, deaerators, stabilizers against oxidation, heat, light or UV radiation, or biocides;

or further substances customarily used in curable compositions.

It may be advisable to chemically or physically dry certain substances before mixing them into the composition.

The curable composition is preferably free of phthalates.

The curable composition preferably contains a content of thixotropic agent of the invention in the range from 1% to 30% by weight, especially 2.5% to 25% by weight.

The content of thixotropic agent of the invention is guided by the desired degree of thixotropization, which depends on the use of the composition in particular.

The curable composition is especially produced with exclusion of moisture and stored at ambient temperature in moisture-tight containers. A suitable moisture-tight container especially consists of an optionally coated metal and/or plastic, and is especially a drum, a transport box, a hobbock, a bucket, a canister, a can, a bag, a tubular bag, a cartridge or a tube.

The curable composition is preferably a one-component moisture-curing composition. Given suitable packaging and storage, it is storage-stable, typically over several months, up to one year or longer.

On application of the composition, the process of curing commences. This results in the cured composition.

In the case of a one-component moisture-curing composition, it is applied as such and then begins to cure under the influence of moisture or water. For acceleration of the curing, an accelerator component which contains or releases water and/or a catalyst can be mixed into the composition on application, or the composition, after application thereof, can be contacted with such an accelerator component.

In the case of a two-component composition, it is applied after the mixing of the two components and begins to cure by internal reaction, and the curing may be completed by the action of external moisture. The two components can be mixed continuously or batchwise with dynamic mixers or static mixers.

In the course of curing, isocyanate groups present react under the influence of moisture with one another and/or with any further reactive groups present in the composition, especially hydroxyl groups or amino groups. In addition, isocyanate groups present react with hydrolyzing reactive groups of any latent curing agents present. Silane groups present react with one another under the influence of moisture in the course of curing. They can be hydrolyzed on contact with moisture to give silanol groups (Si—OH groups). Silane groups present can condense with silanol groups present to give siloxane groups (Si—O—Si groups).

The moisture required for curing of a moisture-curing composition preferably gets into the composition through diffusion from the air (air humidity). In the process, a solid layer of cured composition (skin) is formed on the surfaces of the composition which come into contact with air. The curing continues in the direction of diffusion from the outside inward, the skin becoming increasingly thicker and ultimately encompassing the entire composition applied. The moisture can also get into the composition additionally or entirely from one or more substrate(s) to which the composition has been applied and/or can come from an accelerator component which is mixed into the composition on application or is contacted therewith after application, for example by painting or spraying.

The curable composition is preferably applied at ambient temperature, especially in the range from about −10 to 50° C., preferably in the range from −5 to 45° C., especially 0 to 40° C.

The composition is preferably likewise cured at ambient temperature.

The curable composition has structurally viscous properties, especially an elevated yield point adjustable within a wide range by the thixotropic agent of the invention.

The curable composition may be formulated in such a way that it has a pasty consistency with a high yield point, especially for use as an adhesive or sealant. Such a composition can be applied by spatula or under pressure by means of a suitable device, for example by means of a cartridge gun or a drum pump or an application robot, wherein the composition is especially discharged in the form of a bead having an essentially round or triangular cross-sectional area. When the application device is pulled away, this gives rise only to a very short thread (threading) and hence a low risk of contamination, and the composition has a low viscosity, which means that it can be conveyed with low expenditure of force and hence has good applicability even by means of manual devices, such as mechanical cartridge guns in particular.

The curable composition can also be formulated such that it is only slightly thixotropic, especially for use as sealing compound or coating. Such a composition can be poured out for application or applied by trowel, especially by means of a notched trowel, brick trowel, squeegee or roller. In one operation, typically a layer thickness in the range from 0.5 to 5 mm, especially 1 to 3 mm, is applied.

The thixotropic agent of the invention does not trigger any reactions in the composition that lead to limited usability through increased viscosity, nor does it show any tendency to separation or migration during storage in the container. As a result, the curable composition has very good storage stability. After the composition has been cured, the thixotropic agent remains in the composition. The urea compounds act like a filler in the cured compositions, and the polyether having blocked hydroxyl groups exerts a plasticizing, flexibilizing effect, has no tendency to migration, and causes neither odor nor fogging.

The curable composition is suitable for a multitude of uses.

Preference is given to use as an adhesive or sealant or coating, where the adhesive or sealant or coating is especially elastic.

The composition is especially suitable as an adhesive and/or sealant for bonding and sealing applications, especially in the construction and manufacturing industries or in motor vehicle construction, especially for parquet bonding, installable component bonding, cavity sealing, assembly, module bonding, vehicle body bonding, window pane bonding or joint sealing.

Elastic bondings in motor vehicle construction are, for example, the bonded attachment of parts, such as plastic covers, trim strips, flanges, fenders, driver's cabins or other installable components, to the painted body of a motor vehicle, or the bonding of glass panes into the vehicle body, where the motor vehicles are especially automobiles, trucks, buses, rail vehicles or ships.

The composition is especially suitable as sealant for the elastic sealing of all kinds of joints, seams or cavities, especially of joints in construction, such as expansion joints or connection joints between structural components. A sealant having flexible properties is particularly suitable especially for the sealing of expansion joints in built structures.

As coating, the composition is suitable for the protection of floors or walls, especially as coating of balconies, terraces, open spaces, bridges, parking levels, or for the sealing of roofs, or in the interior of buildings for water sealing, for example beneath tiles or ceramic slabs in wet cells or kitchens, or as seal in collecting tanks, channels, shafts, silos, tanks or wastewater treatment systems, or as seam seal or protective coating for pipes, for example.

It can also be used for repair purposes as seal or coating, for example of leaking roof membranes or floor coverings no longer fit for purpose, or especially as repair compound for highly reactive spray seals.

Suitable substrates which can be bonded or sealed or coated with the composition are especially

- glass, glass ceramic, concrete, mortar, fiber cement, especially fiber cement boards, brick, tile, gypsum, especially gypsum boards, or natural stone, such as granite or marble;
- repair or leveling compounds based on PCC (polymer-modified cement mortar) or ECC (epoxy resin-modified cement mortar);
- metals or alloys, such as aluminum, copper, iron, steel, nonferrous metals, including surface-finished metals or alloys, such as zinc-plated or chromium-plated metals;
- asphalt or bitumen;
- leather, textiles, paper, wood, wood materials bonded with resins, such as phenolic, melamine or epoxy resins, resin/textile composites or further materials called polymer composites;
- plastics, such as rigid and flexible PVC, polycarbonate, polystyrene, polyester, polyamide, PMMA, ABS, SAN, epoxy resins, phenolic resins, PUR, POM, TPO, PE, PP, EPM or EPDM, in each case untreated or surface-treated, for example by means of plasma, corona or flames;
- fiber-reinforced plastics, such as carbon fiber-reinforced plastics (CFP), glass fiber-reinforced plastics (GFP) and sheet molding compounds (SMC);
- insulation foams, especially made of EPS, XPS, PUR, PIR, rock wool, glass wool or foamed glass;
- coated or painted substrates, especially painted tiles, coated concrete, powder-coated metals or alloys or painted metal sheets;
- paints or varnishes, especially automotive topcoats.

If required, the substrates can be pretreated prior to application, especially by physical and/or chemical cleaning methods or the application of an activator or a primer.

It is possible to bond and/or seal two identical or two different substrates.

The application and curing of the composition afford an article.

The invention thus further provides an article bonded or sealed or coated with the composition.

This article may be a built structure above or below ground or part thereof, especially a bridge, a roof, a staircase or a façade, or it may be an industrial good or a consumer good, especially a window, a pipe, a rotor blade of a wind turbine, a domestic appliance or a mode of transport, such as especially an automobile, a bus, a truck, a rail vehicle, a ship, an aircraft or a helicopter, or an installable component thereof.

EXAMPLES

Working examples are adduced hereinafter, which are intended to elucidate the invention described in more detail. The invention is of course not limited to these described working examples.

"Standard climatic conditions" ("SCC") refer to a temperature of 23±1° C. and a relative air humidity of 50±5%.

Unless otherwise stated, the chemicals used were from Sigma-Aldrich Chemie GmbH.

Preparation of Polyethers Having Blocked Hydroxyl Groups:

Viscosity was measured with a thermostated Rheotec RC30 cone-plate viscometer (cone diameter 25 mm, cone angle 1°, cone tip-plate distance 0.05 mm, shear rate 10 s$^{-1}$).

Infrared spectra (FT-IR) were measured as undiluted films on a Nicolet iS5 FT-IR instrument from Thermo Scientific equipped with a horizontal ATR measurement unit with a diamond crystal. The absorption bands are reported in wavenumbers (cm$^{-1}$).

$^1$H NMR spectra were measured on a spectrometer of the Bruker Ascend 400 type at 400.14 MHz; the chemical shifts δ are reported in ppm relative to tetramethylsilane (TMS). No distinction was made between true coupling and pseudo-coupling patterns.

Polyether-1: n-butanol-started acetylated PPG monool with average molecular weight about 800 g/mol 120.00 g of n-butanol-started polyoxypropylene monool (Synalox® 100-20B, average molecular weight about 750 g/mol; from DowDuPont Inc.) and 18.74 g of acetic anhydride were initially charged in a round-bottom flask with distillation attachment under a nitrogen atmosphere. Then the reaction mixture was stirred under a gentle nitrogen stream at 130° C., with collection of acetic acid as distillate. Subsequently, the volatile constituents were removed from the reaction mixture at 80° C. and a reduced pressure of 10 mbar. A clear, colorless liquid having a viscosity of 75 mPa·s at 20° C. was obtained.

FT-IR: 2970, 2931, 2867, 1738, 1454, 1372, 1345, 1296, 1241, 1098, 1014, 959, 925, 866, 827.

$^1$H NMR (CDCl$_3$): 5.02 (hept., 1 H, CH$_2$(CH$_3$)CH—OAc), 3.75-3.34 (2×m, about 39 H, OCH$_2$CH(CH$_3$)O), 3.33-3.28 (m, 2H, CH$_3$CH$_2$CH$_2$CH$_2$O), 2.04 (s, 3H, O(CO)CH$_3$), 1.55 (quint., 2 H, CH$_3$CH$_2$CH$_2$CH$_2$O), 1.36 (sext., 2 H, CH$_3$CH$_2$CH$_2$CH$_2$O), 1.22 (d, 3H, CH$_2$(CH$_3$)CH—OAc), 1.17-1.10 (m, about 36 H, OCH$_2$CH(CH$_3$)O), 0.91 (t, 3H, CH$_3$CH$_2$CH$_2$CH$_2$O).

Polyether-2: n-butanol-started polypropylene glycol with 1-(isobutoxy)ethoxy end group and average molecular weight of about 1,200 g/mol 300.00 g of n-butanol-started polyoxypropylene monool with average molecular weight 1,100 g/mol (Synalox® 100-40B, from DowDuPont Inc.) and 0.17 g of methanesulfonic acid (anhydrous) were initially charged in a round-bottom flask under nitrogen atmosphere. Then 28.16 g of isobutyl vinyl ether (stabilized with 0.1% potassium hydroxide) was slowly added dropwise while stirring, such that the temperature of the reaction mixture did not rise above 70° C., and then the mixture was stirred at 70° C. under a nitrogen atmosphere until no hydroxyl groups were detectable any longer by means of IR and GC spectrometry. Subsequently, 0.07 g of sodium methoxide was added and stirred in, followed by 0.06 g of acetic acid. Then the volatile constituents were removed from the reaction mixture, first at 80° C. and a reduced pressure of 5 mbar and then at 100° C. and 2 mbar. A clear, yellowish liquid having a viscosity of 205 mPa·s at 20° C. was obtained.

FT-IR: 2969, 2931, 2868, 1455, 1372, 1344, 1296, 1257, 1099, 1012, 924, 906, 867, 831.

Polyether-3: Diacetylated PPG diol with average molecular weight about 1,100 g/mol 80.00 g of polyoxypropylene diol (Voranol® P 1010, OH number 110 mg KOH/g; from DowDuPont Inc.) and 18.74 g of acetic anhydride were converted as described for polyether-1. A clear, colorless liquid having a viscosity of 145 mPa·s at 20° C. was obtained.

Preparation of Thixotropic Agents:

Thixotropic Agent T-1 (Inventive):

A vacuum mixer was initially charged with 300 g of polyether-1 and 48 g of methylene diphenyl 4,4'-diisocyanate (Desmodur® 44 MC L, from Covestro AG) and heated up slightly, and then 27 g of n-butylamine was slowly added dropwise with vigorous stirring. The resultant paste was stirred for a further hour under reduced pressure while cooling. A white, finely divided, homogeneous, spreadable paste was obtained.

Thixotropic Agent T-2 (Inventive):

Prepared as described for thixotropic agent T-1, except that 300 g of polyether-2 was used in place of polyether-1. A yellowish, finely divided, homogeneous, spreadable paste was obtained.

Thixotropic Agent T-3 (Inventive):

Prepared as described for thixotropic agent T-1, except that 300 g of polyether-3 was used in place of polyether-1. A white, finely divided, homogeneous, spreadable paste was obtained.

Thixotropic Agent T-4 (Comparative Example):

Prepared as described for thixotropic agent T-1, except that 300 g of diisodecyl phthalate (Palatinol® 10-P, from BASF SE) was used in place of polyether-1. A white, finely divided, homogeneous, spreadable paste was obtained.

Thixotropic Agent T-5 (Comparative Example):

Prepared as described for thixotropic agent T-1, except that 300 g of diisononyl cyclohexane-1,2-dicarboxylate (Hexamoll® DINCH, from BASF SE) was used in place of polyether-1. A white, finely divided, homogeneous, spreadable paste was obtained.

Thixotropic Agent T-6 (Comparative Example):

Prepared as described for thixotropic agent T-1, except that 300 g of di(2-ethylhexyl) adipate (Plastomoll® DOA, from BASF SE) was used in place of polyether-1. A white, finely divided, homogeneous, spreadable paste was obtained.

Some thixotropic agents were tested as follows for sag resistance and expression force:

Sag resistance was determined by applying about 8 ml of the paste under standard climatic conditions by means of a cartridge tip with internal diameter 10 mm onto a vertical corrugated cardboard surface so as to result in a nose protruding horizontally for about 50 mm and having a diameter of about 20 mm. After 3 hours, the extent to which the nose had sagged from the horizontal position, measured at the tip, was determined. A sag of less than 2 mm was rated as "good", 2 to 5 mm as "average", and more than 5 mm as "poor".

Expression force (5 mm; 3 mm; 2 mm) was determined by introducing the paste into a standard aluminum cartridge, then screwing on a nozzle having internal diameter 5 mm or 3 mm or 2 mm and using an expression device (Zwick/Roell Z005) to measure the force expended in order to express the thixotropic agent through the respective nozzle at an expression rate of 60 mm/min. The value reported is an average of the forces that were measured after an expression distance of 22 mm, 24 mm, 26 mm and 28 mm.

The results are shown in table 1.

TABLE 1

Properties of thixotropic agents T-1 and T-4.

| Thixotropic agent | T-1 (inventive) | T-4 (comparative example) |
|---|---|---|
| Sag resistance | good | good |
| Expression force [N] | | |
| 5 mm | 518 | 566 |
| 3 mm | 696 | 760 |
| 2 mm | 854 | 951 |

Production of Curable (One-Component) Compositions:

Polymer P1:

590 g of polyoxypropylene diol (Acclaim® 4200, from Covestro AG; OH number 28.5 mg KOH/g), 1180 g of polyoxypropylenepolyoxyethylene triol (Caradol® MD34-02, from Shell Chemicals Co.; OH number 35.0 mg KOH/g) and 230 g of isophorone diisocyanate (Vestanat® IPDI, from Evonik Industries AG) were reacted by a known method at 80° C. to give a polymer containing isocyanate groups which is liquid at room temperature and has a content of free isocyanate groups of 2.1% by weight.

Polymer P2:

400 g of polyoxypropylene diol (Acclaim® 4200, from Covestro AG; OH number 28.5 mg KOH/g) and 52 g of diphenylmethane 4,4'-diisocyanate (Desmodur® 44 MC L, from Covestro AG) were reacted by a known process at 80° C. to give an NCO-terminated polymer which is liquid at room temperature and has a content of free isocyanate groups of 1.85% by weight.

Polymer P3:

3080 g of polyoxypropylene diol (Acclaim® 4200, from Covestro AG; OH number 28.5 mg KOH/g), 1540 g of polyoxypropylenepolyoxyethylene triol (Caradol® MD34-02, from Shell Chemicals Co.; OH number 35.0 mg KOH/g) and 385 g of tolylene diisocyanate (Desmodur® T 80 P, Covestro AG) were reacted at 80° C. by a known method to give an NCO-terminated polyurethane polymer which is liquid at room temperature and has a content of free isocyanate groups of 1.5% by weight.

Aldimine-1: N,N'-Bis(2,2-dimethyl-3-lauroyloxypropylidene)-3-aminomethyl-3,5,5-trimethylcyclohexylamine 598 g (2.1 mol) of 2,2-dimethyl-3-lauroyloxypropanal was initially charged in a round-bottom flask under a nitrogen atmosphere. Then 170.3 g (1 mol) of 3-aminomethyl-3,5,5-trimethylcyclohexylamine (Vestamin® IPD, from Evonik Industries AG) was added with good stirring, and then the volatile constituents were removed at 80° C. and a reduced pressure of 10 mbar. 732 g of a colorless liquid having an amine content of 2.73 mmol N/g was obtained, corresponding to a calculated aldimine equivalent weight of 367 g/mol.

Compositions Z1 and Z2

For each composition, the ingredients specified in table 2 were mixed in the amounts specified (in parts by weight) by means of a centrifugal mixer (SpeedMixer™ DAC 150, FlackTek Inc.) with exclusion of moisture at 3000 rpm for one minute.

Sag resistance of each composition was determined by applying about 8 ml of the composition under standard climatic conditions by means of a cartridge tip with internal diameter 10 mm onto a vertical corrugated cardboard surface so as to result in a nose protruding horizontally for about 50 mm and having a diameter of about 20 mm. After curing under standard climatic conditions, the extent to which the nose had sagged from the horizontal position, measured at the tip, was determined. A sag of less than 15 mm was rated as "good", 15 to 30 mm as "average", and more than 30 mm as "poor".

The results are reported in table 2.

Compositions labeled "(Ref.)" are comparative examples.

TABLE 2

Composition (in parts by weight) and properties of Z1 and Z2.

| Composition | Z1 | Z2 (Ref.) |
|---|---|---|
| Polymer P1 | 200.0 | 200.0 |
| Thixotropic agent | T-1 | T-4 |
|  | 200.0 | 200.0 |
| Sag resistance | good | good |

Compositions Z3 to Z6

For each composition, the ingredients specified in table 3 were mixed in the amounts specified (in parts by weight) by means of a centrifugal mixer (SpeedMixer™ DAC 150, FlackTek Inc.) with exclusion of moisture at 3000 rpm for one minute.

For each composition, formation of specks on cardboard was determined as a measure of plasticizer migration. For this purpose, each composition was applied to a piece of cardboard such that it had a round base area of diameter 15 mm and a height of 4 mm, and was stored under standard climatic conditions for 7 days. Around each composition, thereafter, a dark oval stain had formed on the cardboard. The dimensions thereof (height and width) were measured and reported in table 3 as Migration.

Compositions labeled "(Ref.)" are comparative examples.

TABLE 3

Composition (in parts by weight) and properties of Z3 to Z6.

| Composition | | Z3 | Z4 (Ref.) | Z5 (Ref.) | Z6 (Ref.) |
|---|---|---|---|---|---|
| Polymer P2 | | 80.00 | 80.00 | 80.00 | 80.00 |
| Chalk¹ | | 80.00 | 80.00 | 80.00 | 80.00 |
| Thixotropic agent | | T-1 | T-4 | T-5 | T-6 |
|  | | 115.9 | 115.9 | 115.9 | 115.9 |
| 2,2'-Dimorpholinodiethylether | | 0.26 | 0.26 | 0.26 | 0.26 |
| Migration | Height | 0.5 | 0.5 | 1 | 3 |
| (7 d) mm | Width | 1 | 1 | 2 | 4 |

¹Omyacarb ® 5 GU (from Omya AG)

Compositions Z7 to Z9

For each composition, the ingredients specified in table 4 were mixed in the amounts specified (in parts by weight) by means of a centrifugal mixer (SpeedMixer™ DAC 150, FlackTek Inc.) with exclusion of moisture at 3000 rpm for one minute and stored with exclusion of moisture.

Each composition was tested as follows:

Sag resistance was determined as described for composition Z1. An assessment was additionally made as to whether a long thread was drawn when the application tool was pulled away after the application of the "nose". If no thread formed, but rather a short tip of less than 10 mm, threading was assessed as "no".

As a measure of the open time, skin time (ST) was determined. For this purpose, a few grams of the composition was applied to cardboard in a layer thickness of about 2 mm and, under standard climatic conditions, the first period of time after which no residues remained any longer on an LDPE pipette used to gently tap the surface of the composition was determined.

Shore A hardness was determined to DIN 53505 on test specimens cured under standard climatic conditions for 14 days.

To determine the mechanical properties, the composition was applied to a PTFE-coated film to give a film of thickness 2 mm, the film was stored under standard climatic conditions for 14 days, and a few dumbbells having a length of 75 mm with a bar length of 30 mm and a bar width of 4 mm were punched out of the film and these were tested in accordance with DIN EN 53504 at a strain rate of 200 mm/min for Tensile strength (breaking force), Elongation at break, Modulus of elasticity 5% (at 0.5%-5% elongation) and Modulus of elasticity 25% (at 0.5%-25% elongation).

Appearance was assessed visually on the films produced. "Nice" was used to describe a nontacky film without blisters.

Odor was assessed by smelling by nose at a distance of 2 cm from the freshly produced films. "No" means that no odor was perceptible.

The results are reported in table 4.

TABLE 4

Composition (in parts by weight) and properties of Z7 to Z9.

| Composition | Z7 | Z8 | Z9 |
|---|---|---|---|
| Polymer P3 | 28.00 | 28.00 | 28.00 |
| Aldimine-1 | 2.58 | 2.58 | 2.58 |
| Polyether-1 | 14.00 | — | — |
| Polyether-2 | — | 14.00 | — |
| Polyether-3 | — | — | 14.00 |
| Thixotropic agent | T-1 | T-2 | T-3 |
|  | 20.00 | 20.00 | 20.00 |
| Chalk ¹ | 33.89 | 33.89 | 33.89 |
| Salicylic acid solution ² | 1.50 | 1.50 | 1.50 |
| Dibutyltin dilaurate | 0.03 | 0.03 | 0.03 |
| Sag resistance | good | good | good |
| Threading | no | no | no |
| ST [min] | 25 | 25 | 25 |
| Shore A | 10 | 9 | 16 |
| Tensile strength [MPa] | 1.14 | 1.22 | 1.37 |
| Elongation at break [%] | 809 | 776 | 784 |
| Modulus of elasticity 5% [MPa] | 0.52 | 0.44 | 0.54 |
| Modulus of elasticity 25% [MPa] | 0.26 | 0.26 | 0.45 |
| Appearance | nice | nice | nice |
| Odor | no | no | no |

¹ Omyacarb ® 5-GU (from Omya AG)
² 5% by weight in di(2-ethylhexyl) adipate

The invention claimed is:

1. A thixotropic agent for increasing the yield point of a curable composition, wherein the thixotropic agent comprises (i) at least one urea compound from the reaction of at least one isocyanate with at least one amine and (ii) at least one polyether having blocked hydroxyl groups which is free of urethane groups.

2. The thixotropic agent as claimed in claim 1, wherein the at least one urea compound has the formula (I)

$$E-\underset{H}{N}-\overset{O}{\overset{\|}{C}}-\underset{H}{N}-Q-\underset{H}{N}-\overset{O}{\overset{\|}{C}}-\underset{H}{N}-E \qquad (I)$$

where
E is an alkyl or cycloalkyl radical having 1 to 12 carbon atoms, and
Q is a divalent hydrocarbyl radical having 6 to 15 carbon atoms.

3. The thixotropic agent as claimed in claim 1, wherein the thixotropic agent takes the form of a spreadable paste which is firm at room temperature.

4. The thixotropic agent as claimed in claim 1, wherein 5% to 25% by weight of urea compounds and 50% to 95% by weight of polyethers having blocked hydroxyl groups are present.

5. The thixotropic agent as claimed in claim 1, wherein the at least one polyether having blocked hydroxyl groups has a viscosity at 20° C. in the range from 30 to 500 mPa·s, where the viscosity is determined with a cone-plate viscometer having cone diameter 25 mm, cone angle 1°, cone tip-plate distance of 0.05 mm, at a shear rate of 10 s$^{-1}$.

6. The thixotropic agent as claimed in claim 1, wherein the at least one polyether having blocked hydroxyl groups has an average of 1 to 3 blocked hydroxyl groups per molecule.

7. The thixotropic agent as claimed in claim 1, wherein the blocked hydroxyl groups are selected from the group consisting of acetal, ester, aceto ester and carbonate groups.

8. The thixotropic agent as claimed in claim 1, wherein 70% to 100% by weight of the repeat units in the at least one polyether having blocked hydroxyl groups consist of 1,2-propyleneoxy groups, and 0% to 30% by weight of the repeat units in the at least one polyether having blocked hydroxyl groups consists of 1,2-ethyleneoxy groups.

9. The thixotropic agent as claimed in claim 1, wherein the at least one polyether having blocked hydroxyl groups has an average molecular weight $M_n$ in the range from 600 to 2,500 g/mol, determined by means of gel permeation chromatography versus polystyrene as standard with tetrahydrofuran as mobile phase, refractive index detector and evaluation from 200 g/mol.

10. The thixotropic agent as claimed in claim 1, wherein the at least one polyether having blocked hydroxyl groups is derived from at least one hydroxy-functional polyether selected from the group consisting of
  alcohol-started, polyoxypropylene monools having an OH number in the range from 25 to 90 mg KOH/g,
  polyoxypropylene diols having an OH number in the range from 45 to 155 mg KOH/g and
  trimethylolpropane-started, optionally ethylene oxide terminated, polyoxypropylene triols having an average OH functionality in the range from 2.2 to 3 and an OH number in the range from 90 to 230 mg KOH/g.

11. A preparation of the thixotropic agent as claimed in claim 1, wherein the reaction between the at least one isocyanate and the at least one amine is performed in the at least one polyether having blocked hydroxyl groups.

12. A method comprising applying the thixotropic agent as claimed in claim 1 in a curable composition for increasing the yield point of the curable composition.

13. A curable composition comprising the thixotropic agent as claimed in claim 1 and at least one polymer containing isocyanate and/or silane groups.

14. The curable composition as claimed in claim 13, wherein it is a one-component moisture-curing composition.

15. An article bonded or sealed or coated with the curable composition as claimed in claim 13.

\* \* \* \* \*